United States Patent [19]

Brocks et al.

[11] Patent Number: 5,147,782
[45] Date of Patent: Sep. 15, 1992

[54] PROCESS FOR THE ISOLATION OF BASEMENT MEMBRANE PROTEINS FROM HUMAN AND ANIMAL TISSUES

[75] Inventors: Dietrich Brocks, Wiesbaden; Rupert Timpl, Gauting; Mats Paulsson, Martinsried, all of Fed. Rep. of Germany

[73] Assignee: Hoechst Aktiengellschaft, Frankfurt am Main, Fed. Rep. of Germany

[21] Appl. No.: 167,177

[22] Filed: Mar. 11, 1988

[30] Foreign Application Priority Data

Mar. 13, 1987 [DE] Fed. Rep. of Germany ....... 3708198

[51] Int. Cl.$^5$ .................... G01N 33/567; C12N 9/99
[52] U.S. Cl. .................................. 435/7.21; 435/7.1; 435/23; 435/184; 435/803; 435/820; 435/961; 435/962; 436/63; 436/177; 436/811; 436/825; 530/412
[58] Field of Search .................. 435/7, 123, 184, 7.21, 435/803, 820, 961, 962, 7.1; 436/50, 63, 177, 811, 825; 530/412, 413, 350

[56] References Cited

U.S. PATENT DOCUMENTS 4,628,027 12/1986 Gay .................................. 436/506

FOREIGN PATENT DOCUMENTS 1155757 7/1986 Japan ................................. 436/825

OTHER PUBLICATIONS

Dziadek et al., Biological Abstracts, vol. 80(5), 1985, Abstract No. 40294.
Dziadek et al., "Purification and Tissue Distribution of a Small Protein (BM-40) Extracted From a Basement Membrane Tumor", European Journal of Biochemistry 161:455–464 (1986).
Ohno et al., "Isolation of Laminin from Human Placental Basement Membranes: Amnion, Chorion and Chorionic Microvessels", Biochemical and Biophysical Research Communications, 112:1091–1098 (1983).
Paulsson et al., "Purification and Structural Characterization of Intact and Fragmented Nidogen Obtained from a Tumor Basement Membrane", European Journal of Biochemistry 156:467–478 (1986).
Risteli et al, "Isolation and Characterization of Pepsin Fragments of Laminin from Human Placental and Renal Basement Membranes" Biochemistry Journal 193:749–755 (1980).
Timpl et al., "Laminin—A Glycoprotein from Basement Membranes", The Journal of Biological Chemistry 254:9933–9937 (1979).
Wewer et al, "Human Laminin Islated in a Nearly Intact, Biologically Active Form from Placenta by Limited Proteolysis", The Journal of Biological Chemistry 258:12654–12660 (1983).
Vincent et al., Biological Abstracts, vol. 72(1), Abstract No. 2537, 1981.
Victoria et al., Biological Abstracts, vol. 72(12), Abstract No. 78502, 1981.

Primary Examiner—Esther L. Kepplinger
Assistant Examiner—Toni R. Scheiner
Attorney, Agent, or Firm—Finnegan, Henderson, Farabow, Garrett and Dunner

[57] ABSTRACT

Basement membrane proteins are isolated as functioning proteins in relatively large amounts from human or animal tissues in aqueous solution in the presence of a chelating agent. It is possible to use these proteins to obtain highly specific antibodies which are used for the immunological determination of these proteins.

7 Claims, No Drawings

PROCESS FOR THE ISOLATION OF BASEMENT MEMBRANE PROTEINS FROM HUMAN AND ANIMAL TISSUES

Laminin, nidogen and BM40 are glycoproteins which are attributed with a key role in the organization of basement membranes and in the interaction of cells with basement membranes [Paulsson, M. et al. Eur. J. Biochem. 161, 455–464 (1986), R. Timpl, M. Dziadek, Int. Rev. Exp. Pathol. 29, 1–112 (1986)]. Thus, laminin assists the outgrowth of axons from the neurones of peripheral nerves [Edgar, D. et al., EMBO J. 3, 1463–1467 (1984)]and the regeneration thereof in situ [Madison et al. Exp. Neurol. 88, 767–772 (1985)].

Wider use of these proteins has hitherto been prevented in particular by the unavailability of suitable processes which allow these proteins to be isolated from human tissue in a non-damaging manner. The process described by Risteli and Timpl [Biochem. J. 193, 749–755 (1981)]deals with the isolation of the protease-resistant laminin fragment P1 from human placenta. This fragment no longer contains the domain 8 which is important for the interaction with nerves and tumor cells. It is not possible by use of the process described by Timpl et al. [J. Biol. Chem. 254, 9933–9937 (1979)]for the isolation of laminin from tumor tissue to solubilize laminin from human placenta, and only low yields are obtained from tumor tissue by this process.

In the process described by Ohno et al. [Biochem. Biophys. Res. Com. 112, 1091–1098 (1983)]and Wewer et al. [J. Biol. Chem. 258, 12654–12660 (1983)]either denaturing conditions or proteolysis are required to extract significant amounts of laminin or laminin fragments from the tissue. It has likewise hitherto been possible to isolate nidogen or BM40 only under denaturing conditions [Dziadek et al., Eur. J. Biochem. 161, 455–464 (1985), Paulsson et al., Eur. J. Biochem. 156, 467–478, (1986)].

It is now possible, using the process according to the invention, to overcome these disadvantages and to isolate biologically active material in a non-damaging manner. Surprisingly, it is possible to extract intact basement membrane proteins from aqueous solution in the presence of a chelating agent and in fact to do so in greater amounts than hitherto possible.

Hence the invention relates to a process for the isolation of basement membrane proteins from human or animal tissues, which comprises extraction of the said tissues in aqueous solution with the addition of a chelating agent.

The invention is explained in detail hereinafter, in particular in the preferred embodiments. The invention is also defined in the patent claims.

It is possible using the process according to the invention to extract all types of human or animal tissue in which basement membrane proteins are found, such as, for example, human placenta, human or animal tumor tissue or the kidneys. It is possible initially to carry out a preliminary extraction. The tissue is homogenized in a buffer which is physiological for basement membrane proteins and in the presence of protease inhibitors, and is centrifuged. Readily soluble proteins, such as serum proteins and cytoplasmic proteins of the tissue, are preferentially removed in this treatment. The tissue residue is then taken up once again in a physiological buffer and is homogenized and extracted in the presence of protease inhibitors and chelate-forming agents. Suitable chelating agents are organic polyacids such as, for example, EDTA, EGTA or citrate. The extraction is carried out with the addition of 1–500 mmol/l of the chelating agent, preferably 10–50 mmol/l, expediently with cooling at 0°–15° C., preferably 4°–10° C. Extraction is still possible at higher temperatures but it is then accompanied by interfering degradation reactions. The extracts contain the desired basement membrane proteins. BM40, nidogen and laminin, in part as a non-covalent complex, are particularly preferably isolated according to the invention.

The individual proteins are isolated from the extract by molecular sieve chromatography on suitable columns such as, for example, dextran, in particular allyl-dextran crosslinked with N,N'-methylenebisacrylamide, or agarose. The final purification of the basement membrane proteins depends on the protein and is preferably carried out on weakly basic ion exchangers followed by molecular sieve chromatography or further purification on agarose or Sepharose columns.

It is possible in this way to isolate amounts of intact basement membrane proteins which are not attained by conventional isolation processes.

The fractionated and purified basement membrane proteins can then each be used as antigens for the preparation of highly specific antisera or antibodies. This is carried out in the customary way by subcutaneous or intramuscular injection in experimental animals, preferably in rabbits. This is expediently carried out in the presence of complete Freund's adjuvant. The antigen doses customary in these cases can be used. The preferred dose for rabbits is 0.5 to 1 mg per animal. The antiserum which has formed is then obtained in a manner known to the expert and can be used as such. It is also possible previously to purify the antibodies present in the serum. A preferred method for this is affinity chromatography.

The highly specific antiserum prepared using the purified basement proteins makes it possible to determine basement membrane proteins in body fluids such as, for example, serum, urine etc. and tissue extracts by use of immunological detection methods known per se.

It is possible to use for these determinations both the known radioimmunoassay (RIA) variants and the enzyme immunoassay variants and analogous methods.

The labeling of the antigen which is necessary for the immunological determination can be carried out by methods known for protein labeling. Radioactive, enzyme or fluorescence labels are preferably used. In the case of radioactive labeling, the radionuclide which is preferably used is iodine-125. The labeling can then be carried out by the known chloramine T method (Int. Arch. Allergy 29, 185, 1966).

In these detection reactions, the labelled basement membrane protein competes in a known manner for the antibody so that the amount of labelled antigen in the antigen-anti-body complex which is formed decreases as the amount of unlabelled antigens contained in the sample which is to be determined increases. It is possible to employ either the labeling of the complex, for example the radioactivity or the enzyme activity, or the labeling of the supernatant after removal of the antigen-antibody complex, in order to establish, by means of a calibration plot which has been constructed using samples of known content of basement membrane protein, the amounts of antigen contained in the sample to be investigated. The labeling in the complex is preferably determined.

A preferred embodiment of the method according to the invention comprises carrying out the removal of the anti-gen-antibody complex, which has formed with the specific antiserum, by use of a second antibody. Preferably employed for this purpose is an antibody which is directed against immunoglobulin G of the species used for obtaining the specific antiserum. The antigen-antibody complex can be removed from the solution using methods customary for this purpose, such as precipitation, centrifugation or filtration. As an alternative to this, the antiserum or the second antibody is bound to a solid carrier. Then, after removal of the antigen-antibody complex, the radio-activity or other labeling contained in the complex or remaining in the solution is determined.

The enzyme immunoassay variant for the determination of basement membrane protein can also be carried out in such a way that the antibody against immunoglobulin G of the relevant species, for example from the rabbit, is enzyme-labeled. In this type of enzyme immunoassay the portion of the anti-basement membrane protein serum remaining after formation of the antigen-antibody complex is determined by binding this portion to carrier-bound basement membrane protein and then reacting it with enzyme-labeled antibodies against rabbit immunoglobulin G. The amount of bound enzyme-labeled antibody is then determined by measurement of the enzyme reaction and is inversely proportional to the unknown amount of basement membrane protein in the sample.

The invention is explained further in the Examples which follow.

EXAMPLE 1

Isolation of the Basement Membrane Proteins Laminin, nidogen and BM40

EHS tumor cells were injected subcutaneously into C57Bl mice [Orkin et al. J. Exp. Med. 145. 204 (1977)]. The tumor is harvested after 10-14 days, and the tissue material which is then purified is stored at −20° C. 75 g of the frozen tumors were homogenized in 1.5 1 of 0.15M NaCl, 0.05 M Tris-HCl (pH 7.4) (TBS) with 0.05 mM phenyl-methanesulfonyl fluoride (PMSF) and N-ethylmaleimide (NEM) for 1 min. After centrifugation at 8,000 r.p.m. for a period of 20 min the supernatant was discarded and the residue was again homogenized in 375 ml of the above-mentioned buffer with the addition of 10 mM EDTA and stirred in a cold room for one hour. The extract was obtained after the centrifugation indicated above, and was either used further immediately or stored at −20° C. It was possible to increase further the yield and purity of the desired product if the extraction steps were repeated.

An aliquot of the TBS/EDTA extract was passed through an agarose (®Biogel A5m) or a Sepharose CL-6B column (3×135 cm) which had been equilibrated in TBS containing 2mM EDTA, 0.5 mM PMSF and 0.5 mM NEM. This resulted in splitting up into 3 to 4 fractionation ranges. The material eluted first in the exclusion volume contains laminin/nidogen complex and free laminin, and the subsequent fractions contain free nidogen in intact (MW 150 KD) and partially degraded form (MW 130 and 100 KD). BM 40 is eluted subsequently.

The laminin is purified first on a weakly basic ion exchanger (DEAE-cellulose) using 2M urea in 0.05M Tris-HCl (pH 8.6) with the addition of protease inhibitors. A linear NaCl gradient (0 to 0.4M) is used for elution. In this step interfering contamination by proteoglycan and nucleic acids is removed. Finally, remaining nidogen and smaller proteins are removed from laminin by chromatography on Sepharose CL-4B in 2M guanidinium chloride (pH 7.4).

Nidogen is purified first on DEAE-celluose and Sepharose CL-4B as described for laminin. Where necessary, further purification steps entail chromatography on CM-cellulose with 2M urea, 0.02M Na-acetate (pH 4.8) and crosslinked allyldextran (Sephacryl S200) with 0.2 M $NH_4HCO_3$.

Further purification of BM40 is likewise carried out on DEAE-cellulose with 2M urea, 0.05M Tris (pH 8.6), eluting with a linear NaCl gradient (0–0.4M NaCl). BM40 elutes at 0.2–0.25M NaCl and is finally purified after concentration on Sephacryl S200 with 0.2M $NH_4HCO_3$.

The Table shows, by way of example, that the amounts of intact basement membrane proteins extracted from, for example, EHS tumor using the non-damaging extraction are such as cannot be achieved with conventional processes.

TABLE

|  | Protein found in mg per g wet weight | | |
|---|---|---|---|
|  | Laminin | Nidogen | BM40 |
| TBS extract | 0.98 | 0.05 | 0.07 |
| TBS/EDTA extract | 2.84 | 0.46 | 0.34 |
| 0.5 M NaCl | 0.39 | <0.05 | not determined |
| 6 M guanidinium chloride | 0.83 | 0.30 | <0.01 |

EXAMPLE 2

Preparation of the Labeled Antigen

25 μg of the basement membrane protein isolated as in Example 1 are labeled with 0.5 mCi of iodine-125 by the chloramine T method, and unbound iodine is removed by dialysis or gel filtration on a polyacrylamide gel (for example ®Biogel P2, Pharmacia Fine Chemicals Inc.).

EXAMPLE 3

Procedure for the Immunological Determination

All the steps necessary for the immunological determination are carried out in the presence of 0.04% of a non-ionic detergent such as, for example, Tween 20, a polyethoxylated sorbitan monolaurate. Binding plots are determined using 1 ng of labeled basement membrane protein isolated as in Example 1. The concentration of basement membrane protein in an unknown sample of serum or other body fluids is determined in the following inhibition assay:

A defined amount of the specific antibody or antiserum is preincubated with the unknown sample at 4° C. for 16 h and, after addition of 1 ng of labeled antigen, incubation at 4° C. is continued for 8 hours. An excess of antibodies against rabbit immunoglobulin G is then added and, after a further 16 h at 4° C., the antigen bound in the immune complex is removed by centrifugation. The inhibitory activity of the unknown sample is compared with the activity of a standard concentration of unlabeled antigen.

EXAMPLE 4

Preparation of the Antiserum

Rabbits are immunized with 0.5 to 1 mg per animal of the basement membrane protein isolated as in Example 1, by subcutaneous or intramuscular injection of the antigen solution mixed with the same volume of complete Freund's adjuvant. 4 weeks after the first injection, an equal amount of antigen solution mixed with complete Freund's adjuvant is injected subcutaneously or intramuscularly. 4 to 8 weeks after the second injection, blood is collected and from this, after coagulation, the antiserum is obtained.

We claim:

1. A process for extracting basement membrane proteins from human or animal tissue, which comprises the following steps:
   (a) preextracting basement membrane containing tissue in the presence of a protease inhibitor in a physiological buffer which preserves the natural conformation of the basement membrane proteins; and
   (b) extracting the basement membrane proteins from human or animal tissue in the presence of a protease inhibitor and a chelating agent in a buffer which preserves the natural conformation of the basement membrane proteins.

2. The process as claimed in claim 1, wherein the extraction is carried out in the presence of chelate-forming organic polyacids.

3. The process as claimed in claim 2, wherein the extraction is carried out in the presence of EDTA or EGTA.

4. The process as claimed in claim 1, wherein the extraction is carried out in the presence of 1 to 500 mM of the chelating agent.

5. The process as claimed in claim 4, wherein the extraction is carried out in the presence of 10 to 50 mM of the chelating agent.

6. A method for the immunological determination of basement membrane proteins in a sample of body fluid or tissue extract comprising the steps of extracting basement membrane proteins from tissue in the presence of a protease inhibitor in a physiological buffer which preserves the natural conformation of the basement membrane proteins and which contains a chelating agent, preparing a highly specific antisera or antibodies to the isolated basement membrane proteins and thereafter incubating the sample with the antisera or antibodies and detecting specific binding of the antisera or the antibodies to immunologically determine the concentration of basement membrane proteins in the sample.

7. The method of claim 6 further comprising, before the extraction step, pre-extracting the tissue in a physiological buffer which preserves the natural conformation of the basement membrane proteins in the presence of a protease inhibitor.

* * * * *